(12) United States Patent  
Mangiarini

(10) Patent No.: US 8,992,107 B2
(45) Date of Patent: Mar. 31, 2015

(54) ORAL CAVITY CLEANING DEVICE

(76) Inventor: Luigi Mangiarini, Concesio (IT)

( * ) Notice: Subject to any disclaimer, the term of this patent is extended or adjusted under 35 U.S.C. 154(b) by 913 days.

(21) Appl. No.: 13/061,951

(22) PCT Filed: Sep. 4, 2009

(86) PCT No.: PCT/IB2009/053864
§ 371 (c)(1),
(2), (4) Date: Mar. 11, 2011

(87) PCT Pub. No.: WO2010/026548
PCT Pub. Date: Mar. 11, 2010

(65) Prior Publication Data
US 2011/0158739 A1 Jun. 30, 2011

(30) Foreign Application Priority Data

Sep. 8, 2008 (IT) ............... BS2008A0167

(51) Int. Cl.
*A47L 13/22* (2006.01)
*A61C 15/02* (2006.01)
*A46B 5/00* (2006.01)
*A46B 11/00* (2006.01)
*A46B 15/00* (2006.01)

(52) U.S. Cl.
CPC ............... *A61C 15/02* (2013.01); *A46B 5/0095* (2013.01); *A46B 11/002* (2013.01); *A46B 15/0055* (2013.01); *A46B 15/0069* (2013.01); *A46B 2200/1066* (2013.01)

USPC ............ 401/282; 401/132; 401/284; 401/268

(58) Field of Classification Search
USPC .......... 401/132–135, 268, 282, 285–287, 290
See application file for complete search history.

(56) References Cited

U.S. PATENT DOCUMENTS

| | | | | |
|---|---|---|---|---|
| 1,518,342 A * | 12/1924 | Mendoza | ............ | 401/286 |
| 2,283,781 A * | 5/1942 | Aiken | ............ | 401/135 |
| 3,734,106 A * | 5/1973 | Zimmerman | ............ | 401/284 |
| 4,023,580 A * | 5/1977 | Pieters | ............ | 401/268 |
| 4,155,663 A * | 5/1979 | Cerquozzi | ............ | 401/135 |
| 4,811,445 A * | 3/1989 | Lagieski et al. | ............ | 401/268 |
| 6,030,215 A | 2/2000 | Ellion | | |
| 6,793,433 B2 * | 9/2004 | Giraldo | ............ | 401/270 |
| 6,874,967 B1 * | 4/2005 | Tsaur | ............ | 401/134 |
| 6,932,604 B2 * | 8/2005 | Han et al. | ............ | 401/290 |
| 2005/0232683 A1 | 10/2005 | Zeh | | |

* cited by examiner

Primary Examiner — David Walczak
Assistant Examiner — Bradley Oliver
(74) Attorney, Agent, or Firm — Themis Law

(57) ABSTRACT

An oral cavity cleaning device includes a stem having a mainly longitudinal extension and a pointed profile at a first end; a fluid channel enclosed within the stem and extending along such stem; a fluid reservoir operably connected to the second end of the stem to establish a hydraulic connection with the channel; and a tip having bristles and designed to be removably associated with the first end of the stem, the tip having a plurality of through holes for the passage of fluids from the channel to the area external to the tip, at the bristles.

5 Claims, 1 Drawing Sheet

ORAL CAVITY CLEANING DEVICE

FIELD OF THE INVENTION

The present invention generally finds application to the field of oral hygiene, with particular reference to the devices therefor. More in detail, the present invention relates to a device that can be used for oral cavity cleaning purposes.

BACKGROUND ART

A plurality of oral cavity cleaning devices are available for sale. First, toothbrushes are known, which are simple devices comprising a handle with a bristled head at one end.

The shape of the handle is more or less elaborate in view of a more effective grip and for the head to reach the less accessible zones of the oral cavity. Furthermore, the bristles may also have different shapes and flexibilities for optimized teeth cleaning. The motion of the head in the oral cavity clearly ensures cleaning of the oral cavity and the dental arch.

The use of the toothbrush is usually combined with the use of toothpaste, i.e. a pasty fluid containing ingredients that facilitate removal of bacteria and residues from the oral cavity. Toothpaste also comprises refreshing ingredients to leave a pleasant feel in the user's mouth and to fight halitosis.

A further known device is the tube brush, i.e. a particular toothbrush adapted to ensure hygiene of particularly large interdental spaces and fixed dentures, and to remove the plaque deposited below the elements of a bridge or at the base of the teeth in case of gingival retraction.

Another currently available instrument that may be used for cleaning the oral cavity is the toothpick. This is known to be a small object with at least one pointed end, for at least partial penetration of dental and/or gingival interstices to engage and remove food residues or else.

When regularly and properly used, the above devices are aids to oral cavity cleaning and hygiene. An additional aid is known to be the use of gargles.

Nevertheless, while the above mentioned devices and fluids are available in large numbers, none of them, if used alone, can reach more than partial results in oral cavity hygiene care.

For instance, the tube brush is not suitable for use with toothpaste, and the toothbrush, due to the flexibility of its bristles, cannot be an effective substitute for the tube brush or the toothpick. On the other hand, while the tube brush is of relatively small size, it is larger than a tooth pick, which can reach food residues even in particularly narrow interstices.

US2005/232683 discloses an oral cavity cleaning device having all the features of the preamble of claim 1, with a reservoir enclosed into a stem which could be filled and/or refilled with a fluid for cleaning the oral cavity. However, this known device is adapted to be used only as a toothbrush.

SUMMARY OF THE INVENTION

The object of the present invention is to at least partially overcome the above mentioned drawbacks by providing an oral cavity cleaning device that at least partially obviates the prior art drawbacks.

More in detail, one object of the present invention is to provide a device that allows teeth cleaning by bristles, as well as removal of food residues even from the narrowest interstices.

Another object of the present invention is to provide a device that allows delivery of fluids containing antiseptic ingredients and/or phytotherapeutic preparations to the oral cavity.

In other words, one object of the invention is to provide a device that allows full cleaning of the oral cavity by combining at least the features of a toothbrush, a toothpaste, a gargle, a tube brush and a toothpick.

A further object is to provide a device that both hygienizes and provides a cool and fresh feeling to the whole oral cavity.

Another object is to provide a device that is easy to make and easy to use, allowing total replacement of the plurality of prior art devices and fluids as described above.

These and other objects, as more clearly explained hereafter, are fulfilled by an oral cavity cleaning device as described hereinafter. Further advantageous embodiments of the invention are defined by the dependent claims.

In one aspect of the invention, the oral cavity cleaning device may comprise at least one stem having a mainly longitudinal extension and a substantially pointed profile at a first end thereof. In other words, the stem may be advantageously used as a toothpick. For this purpose, in another aspect of the invention, the stem may have a substantially filiform shape.

In another aspect of the invention, the stem may include at least one fluid channel. This allows delivery of refreshing, antibacterial, phytotherapeutic fluids, gargles or the like to the oral cavity.

Thus, the device of the invention may conveniently include at least one fluid reservoir.

In a further aspect of the invention, the device may have at least one bristled tip, designed for association with the first end of the stem. Such tip may have a plurality of through holes for the passage of fluids from the channel to the area external to the tip, at the bristles. This allows the above fluids, as well as toothpaste or the like, to be delivered to the bristles.

BRIEF DESCRIPTION OF THE DRAWINGS

Further features and advantages of the invention will be more readily apparent from the detailed description of a few preferred, non exclusive embodiments of an oral cavity cleaning device of the invention, which are shown as non limiting examples with the help of the annexed drawings, in which.

DETAILED DESCRIPTION OF ONE PREFERRED EMBODIMENT

Figures 1, 2:
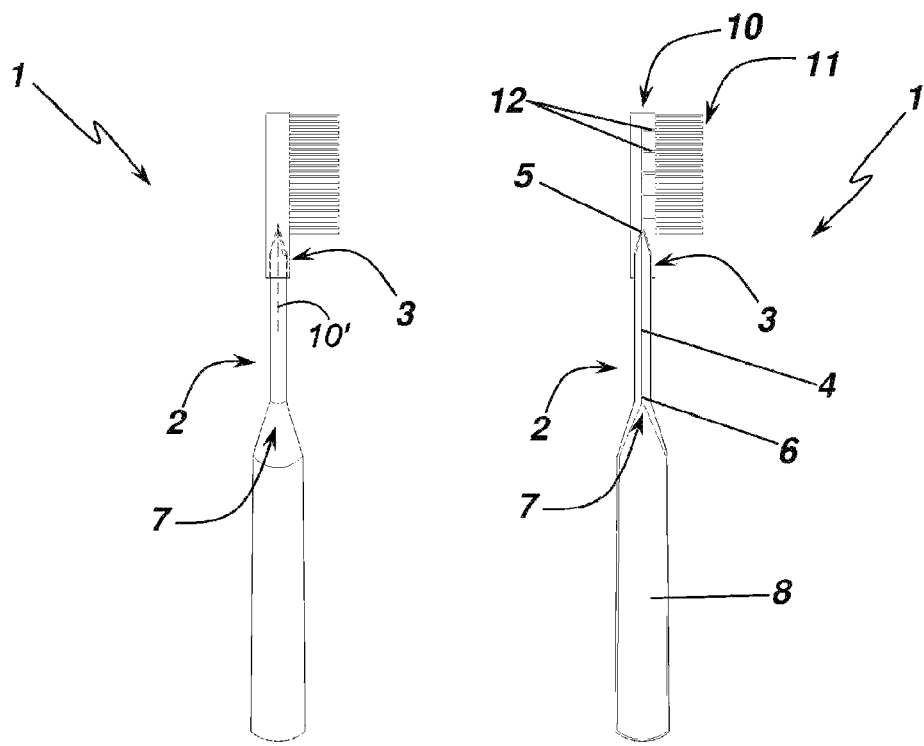
FIG. 1 is a perspective view of a device according to the invention.
FIG. 2 is a broken away view of the device of FIG. 1.

Referring to the above figures, there is disclosed an oral cavity cleaning device 1 comprising at least one stem 2 having a mainly longitudinal extension and a substantially pointed profile at a first end 3 thereof.

Thus, as anticipated above, the first end 3 of the stem 2 can be advantageously used as a toothpick. This feature is enhanced by the provision of a substantially filiform stem 2.

This stem encloses at least one fluid channel 4 extending along the stem 2. Particularly, the channel 4 has a pair of apertures 5 and 6 at the first 3 and second 7 ends of the stem 2 respectively.

Suitably, the second end 7 is mechanically and hydraulically connected to one or more reservoirs 7 containing such fluids. More in detail, the second aperture 6 of the channel 4, which can be found at the second end 7 of the stem 2, is hydraulically connected to the reservoirs 8 for the fluids to be conveyed therefrom to the channel, and from the latter to the oral cavity through the first opening 5 at the first end 3 of the stem 2.

This allows distribution of various types of fluids into the oral cavity through the stem, even when it is used as a toothpick. It will be appreciated that these fluids may contain gargles, refreshing liquids or else.

In another aspect of the invention, the device also has at least one tip with bristles 11, designed for removable association with the first end 3 of the stem 2. Thus, the device 1 of the invention may be also used as a common toothbrush.

Conveniently, the tip 10 has a plurality of through holes 12 for the passage of fluids from the channel 4 through the first aperture 5. These fluids access the oral cavity as they exit the bristled 11 area of the tip 10. The advantages of this embodiment are self-evident if toothpastes containing liquids are used.

It may be appreciated from the above that the device 1 may be considered as a toothbrush with additional tube brush and toothpick features. Also, during use, it may deliver a toothpaste, a gargle, refreshing liquids, antiseptic liquids, phytotherapeutic preparations or else.

This will obviously result in easy use and simple fabrication. Particular advantages are provided by the achievement of total oral cavity cleaning and hygienization results by the use of a single device.

Figure 3:
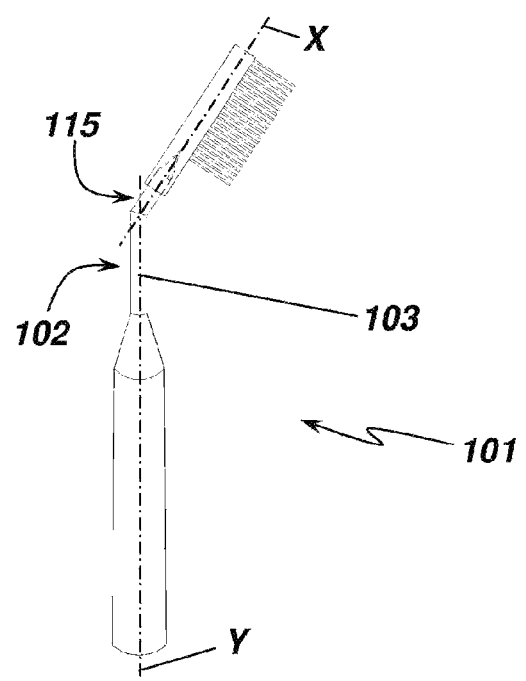
FIG. 3 shows a variant embodiment of the inventive device.

According to a possible embodiment, as shown in FIGS. 1 and 2, the stem 2 has a substantially rectilinear extension. Nevertheless, the stem may be also formed with different shapes for improved effectiveness. For instance, in a variant embodiment, as shown in FIG. 3, at least one terminal portion 115 of the stem 102, at the first end 103, has a longitudinal extension axis X incident on the longitudinal extension axis Y of the rest of the stem 102.

In accordance with another aspect of the invention, the tip 10 has at least one antiobstruction wire 10', susceptible of being inserted at least into the terminal portion of the channel 4 at the first end 3 of the stem 2, to prevent obstruction of such channel with food residues of particularly dense or solidified fluids.

It shall be noted that, since the device 1 of the invention may be used with a plurality of different fluids, the illustrated embodiments of the invention, which show a single reservoir 8, are to be intended without limitation to different embodiments having multiple reservoirs, for the fluids to be held separate before use.

In operation, the user uses the device 1 as a toothbrush, due to the presence of the bristled 11 tip 10. During such use, the user controls the discharge of the toothpaste contained in the reservoirs 8 from the bristles. After such use, the user removes the tip 10 to use the device 1 as a toothpick 1 or a tube brush. It shall be noted that a special tip may be provided in the latter case, that can be fitted to the first end 3 of the stem 2 once the bristled 11 tip 10 has been removed.

During use as a toothpick, the user can control the discharge of refreshing or hygienizing fluids, such as gargles, through the first aperture 5 on the stem 2, to complete oral cavity cleaning and leave a pleasant taste for the user.

After use of the device 1, the user can throw it away or reuse it, by refilling or replacing its reservoirs 8. Similarly, the tips 10 may be also reused or replaced.

In view of the above, the device of the invention fulfils the intended objects. Particularly, the prior art drawbacks have been at least partially obviated by the provision of an oral cavity cleaning device that ensures teeth cleaning by combining the features of a toothbrush, a tube brush and a toothpick.

The device of the invention also allows delivery of fluids containing antiseptic ingredients and/or phytotherapeutic preparations into the oral cavity.

The device of the invention is susceptible of a many changes and variants within the inventive principle as disclosed in the annexed claims. All the details thereof may be replaced by other technically equivalent parts, and the materials may vary depending on different needs, without departure from the scope of the invention. While the device has been described with particular reference to the annexed figures, the numerals referred to in the disclosure and claims are only used for the sake of a better intelligibility of the invention and shall not be intended to limit the claimed scope in any manner.

The invention claimed is:

1. An oral cavity cleaning device comprising:
    a stem having a mainly longitudinal extension with a first end and a second end;
    a channel configured to convey one or more fluids to an oral cavity, said channel being enclosed in said stem;
    a reservoir configured to receive fluids, which is operably connected to the second end of said stem to establish a hydraulic connection with said channel; and
    a tip having bristles and designed to be removably coupled with said first end of said stem, said tip having a plurality of through holes for the passage of said fluids from said channel to an area external to said tip, at said bristles,
    wherein said stem is substantially filiform, said channel extending along said stem and having a pair of apertures at respectively said first end and said second end of said stem,
    wherein said first end has a terminal portion with a longitudinal extension axis, said stem having a substantially pointed profile at said first end,
    wherein said substantially pointed profile is configured for using said first end as a toothpick when said tip is removed, and
    wherein said tip has at least one antiobstruction wire inserted at least into a terminal portion of said channel at said first end of said stem.

2. The device of claim 1, wherein said stem has a substantially rectilinear extension.

3. The device of claim 1, wherein a terminal portion of said stem, at said first end, has a longitudinal extension axis incident on a longitudinal extension axis of a remaining portion of said stem.

4. The device of claim 1, wherein said reservoir is configured to receive one or more antiseptic liquids.

5. The device of claim 1, wherein said reservoir is configured to receive one or more phytotherapeutic preparations.

* * * * *